US00PP22969P2

(12) United States Plant Patent
Egger

(10) Patent No.: US PP22,969 P2
(45) Date of Patent: Aug. 14, 2012

(54) ***KNIPHOFIA* PLANT NAMED 'PINEAPPLE POPSICLE'**

(50) Latin Name: ***Kniphofia* spp.**
Varietal Denomination: Pineapple Popsicle

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/066,149

(22) Filed: Apr. 6, 2011

(51) Int. Cl.
*A01H 5/00* (2006.01)

(52) U.S. Cl. ..... Plt./443

(58) Field of Classification Search ..... Plt./443
See application file for complete search history.

*Primary Examiner* — Annette Para
(74) *Attorney, Agent, or Firm* — Klarquist Sparkman, LLP

(57) ABSTRACT

A new and distinct *Kniphofia* plant characterized by very early blooming, repeat blooming from May through September in Canby, Oreg., compact habit with multiple crowns, yellow buds to cream colored flowers, narrow, grassy leaves, and excellent vigor.

1 Drawing Sheet

Botanical denomination: *Kniphofia* spp.
Cultivar designation: 'Pineapple Popsicle'.

BACKGROUND OF THE INVENTION

The present invention relates to a new and distinct *Kniphofia*, and given the cultivar name is 'Pineapple Popsicle'. *Kniphofia* is in the family Asphodelaceae. *Kniphofia* 'Pineapple Popsicle' is a hybrid resulting from a planned breeding program to produce compact, reblooming *Kniphofia*. The cross was made using the following proprietary, unreleased plants: *Kniphofia* 9-1, as the seed parent, and *Kniphofia* 9-3, as the pollen parent. It was selected for best habit, flower color, reblooming, and crown count from many seedlings in Canby, Oreg.

Compared to *Kniphofia* 'Little Maid', an unpatented plant, the new cultivar is longer blooming, more free flowering, and more vigorous.

SUMMARY OF THE INVENTION

The new cultivar is unique and characterized by:

1. very early blooming (flowers the first year in 30 cell plugs)
2. repeat blooming from May through September in Canby, Oreg.
3. compact habit with multiple crowns
4. narrow, grassy leaves
5. cream to yellow flowers
6. excellent vigor This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a plant of a one-year-old *Kniphofia* 'Pineapple Popsicle' in the ground in the trial in September in Canby, Oreg.

DETAILED PLANT DESCRIPTION

The following is a detailed description of the new *Kniphofia* cultivar based on observations one-year-old specimens grown outside in the trial garden in full sun in Canby, Oreg. The color descriptions are all based on The Royal Horticultural Society Colour Chart, 5$^{th}$ edition.

Plant:
- *Type*.—Rhizomatous herbaceous perennial.
- *Hardiness*.—USDA Zones 6 to 9.
- *Size*.—Grows to 45 cm wide and 44 cm tall from the top of the soil to the top of the foliage.
- *Crown number*.—20. Form — upright and clumping.

Leaf:
- *Type*.—Simple.
- *Shape*.—Strap-like.
- *Arrangement*.—Basal rosette.
- *Blade size*.—Grows to 50 cm long and 16 mm wide.
- *Margins*.—Scabrous.
- *Apex*.—Acuminate.
- *Base*.—Clasping.
- *Surface texture*.—Glabrous on both surfaces.
- *Venation*.—Parallel.
- *Color*.—Top and bottom side Green 137A.

Inflorescence:
- *Type*.—Spike-like scapose raceme.
- *Number of flowers per raceme*.—About 100.
- *Inflorescence*.—17 cm long and 5 cm wide.
- *Peduncle description*.—Grows to 41 cm long and 8 mm wide, glabrous, Yellow Green 146A, tinted Brown 200A.
- *Pedicle description*.—1.5 mm long, glabrous, Yellow Green 146C.
- *Bloom time*.—June to October in Canby, Oreg.
- *Lastingness*.—An inflorescence lasts for 2 to 4 weeks depending on the temperatures.

Flower bud:

*Size*.—25 mm long and 6 mm wide.

*Shape*.—Cylindrical.

*Surface texture*.—Glabrous.

*Color*.—Younger buds Yellow 8C, older buds Yellow 4D.

Flower:

*Type*.—Actinomorphic.

*Shape*.—Cylindrical and tubular.

*Size*.—Grows to 30 mm deep and 10 mm wide.

*Texture*.—Waxy.

*Surface texture*.—Glabrous inside and outside.

*Color*.—Inside and out: Yellow Green 150D with veins Yellow Green 150C.

*Corolla description*.—6 lobed fused tepals, 27 mm long and 10 mm wide, tube 23 mm long and 7 mm wide, lobes each 3 mm wide and 3.5 mm long, ovate, entire, obtuse to acute, glabrous and Yellow Green 150D with veins Yellow Green 150C inside and out.

*Pistil description*.—One, 27 mm long, ovary 3 mm long 2 mm wide, Yellow Green 144A, style 24 mm long, Yellow Green 150C on bottom half to Greyed Orange 164B on top half, stigma White 155A.

*Stamen*.—6, 32 mm long, filaments 30.5 mm long, and White 155A, anthers 1.5 mm long and Yellow Orange 16A, pollen Yellow 8B.

*Fragrance*.—None.

Fruit and seed: None seen.

Pest and diseases: Pests and diseases are infrequent on *Kniphofia* spp. No problems have been observed on this plant grown under commercial conditions in Canby, Oreg.

I claim:

1. A new and distinct *Kniphofia* plant as herein shown and described.

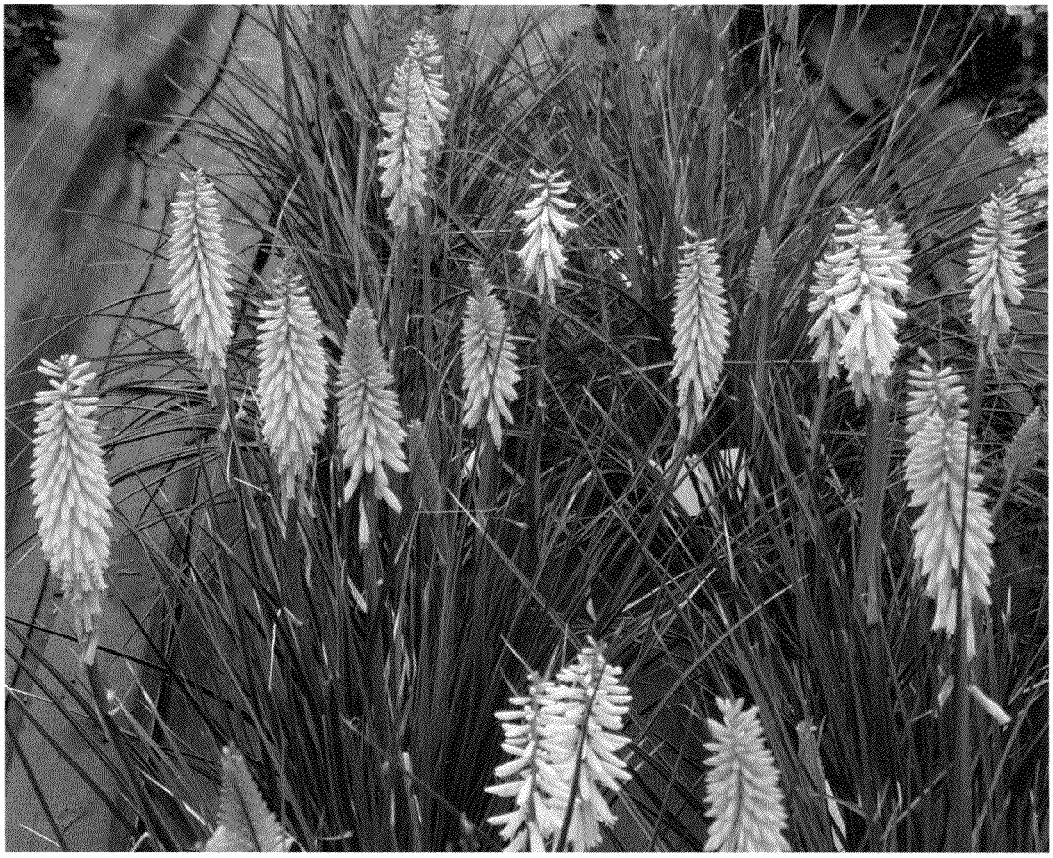

* * * * *